United States Patent [19]

Gatti

[11] Patent Number: 4,865,049
[45] Date of Patent: Sep. 12, 1989

[54] SMOKE ELIMINATING SHIELD FOR ELECTROCAUTERY SURGERY

[76] Inventor: John E. Gatti, 104 Treaty Elms La., Haddonfield, N.J. 08033

[21] Appl. No.: 170,871

[22] Filed: Mar. 21, 1988

[51] Int. Cl.$^4$ ............................................. A61F 13/00
[52] U.S. Cl. .................................... 128/849; 128/910
[58] Field of Search .............. 128/847, 849, 851, 853, 128/855, 857, 200.28, 205.26, 910, 303.17; 98/89

[56] References Cited

U.S. PATENT DOCUMENTS

| | | | |
|---|---|---|---|
| 1,257,332 | 2/1918 | Erlandson | 128/849 |
| 2,032,101 | 2/1936 | Sullivan | 128/200.28 |
| 2,180,480 | 11/1939 | Richardson | 128/205.26 |
| 2,628,803 | 2/1953 | Krewson | 128/847 |
| 3,403,677 | 10/1968 | Struve | 128/847 |
| 3,763,857 | 10/1973 | Schrading | 128/847 |
| 3,820,536 | 6/1974 | Anspach, Jr. et al. | 128/847 |
| 3,877,691 | 4/1975 | Foster | 128/910 |
| 4,055,173 | 10/1977 | Knab | 128/910 |
| 4,223,669 | 9/1980 | Morledge | 128/910 |
| 4,275,719 | 6/1981 | Mayer | 128/849 |

FOREIGN PATENT DOCUMENTS 3859993 1/1975 U.S.S.R. ................. 128/849

Primary Examiner—Robert A. Hafer
Assistant Examiner—Michael Brown
Attorney, Agent, or Firm—Norman E. Lehrer

[57] ABSTRACT

A shield for eliminating smoke created during electrocautery surgery includes an elongated base member and an upwardly extending concave wall secured to one edge thereof. Located on the upper surface of the base member is an elongated suction tube which extends along the base member. A plurality of vertical openings in the upper surface of the tube create an air flow when the tube is connected to a vacuum source. Air and smoke in the vicinity of the shield are drawn inwardly toward the top of the shield, down the inner surface of the concave wall and into the suction tube. The bottom surface of the base member has a pressure sensitive adhesive thereon so that the shield can be mounted on a patient or on the patient's surgical gown or covering adjacent the surgical area.

9 Claims, 2 Drawing Sheets

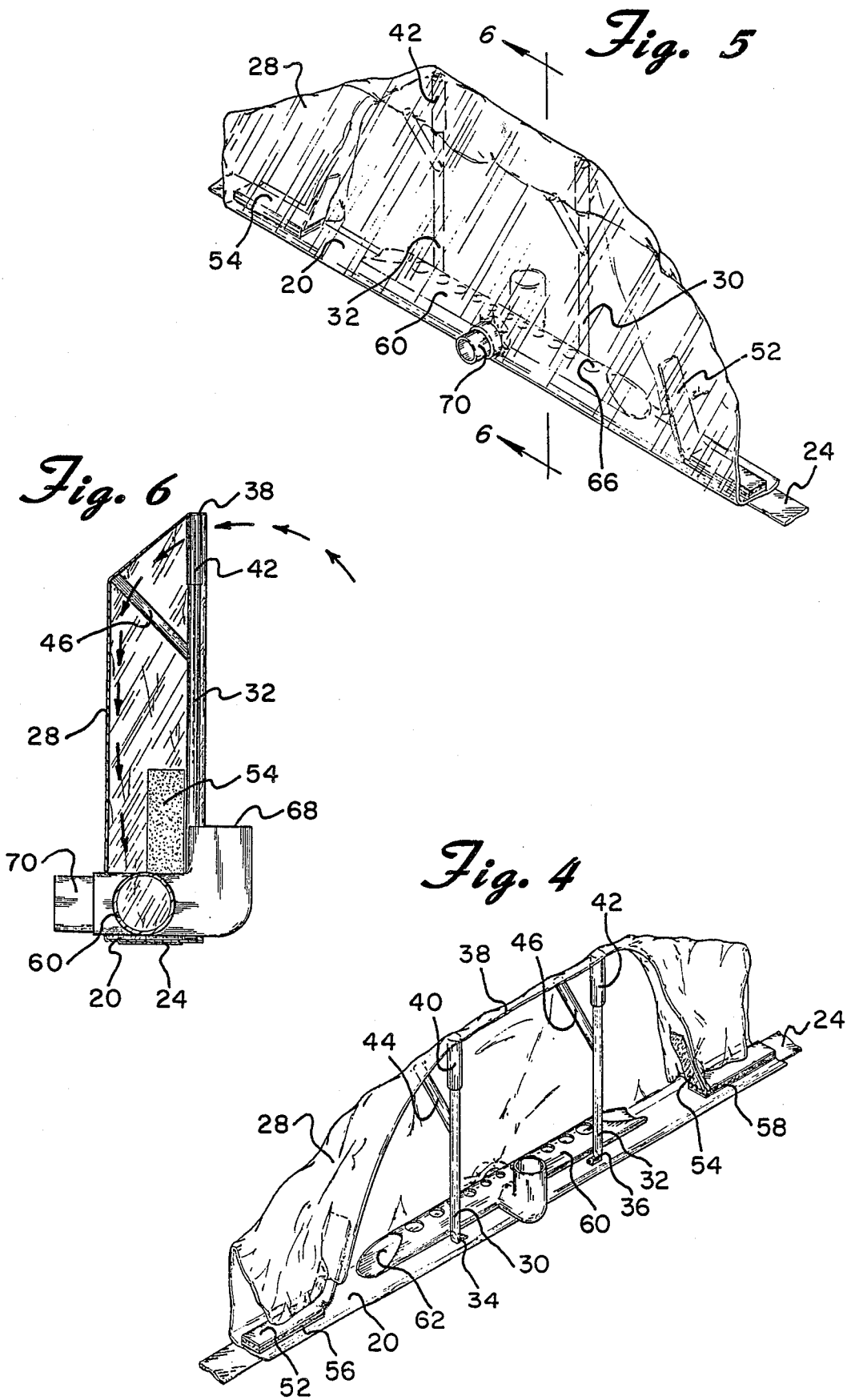

SMOKE ELIMINATING SHIELD FOR ELECTROCAUTERY SURGERY

BACKGROUND OF THE INVENTION

The present invention is directed toward a shield for eliminating smoke generated during electrocautery surgery and more particularly toward such a shield which is simple to use, which does not interfere with the operating surgeon's field of view and which is inexpensive and, therefore, disposable.

As is well known in the art, a significant amount of blood and other tissue fluids and resultant smoke and steam are often present at an electrocautery sight and are generated as a result of the electrocautery surgery. Since their presence can often render it difficult for a surgeon to see the operating sight clearly, devices have been proposed in the past for removing the fluids and smoke.

U.S. Pat. No. 2,888,928 and U.S. Pat. No. 4,307,720, for example, show electrocautery instruments having a suction tube associated therewith and located in close proximity to the cauterizing blade. While such devices may have some usefulness, they are relatively expensive. Because of this, they are intended to be reused and must, therefore, be cleaned and sterilized after each use. Furthermore, these devices are not necessarily intended to be left on at all times but are only turned on when it is desired to remove heavy accumulations of fluid or smoke. Thus, when the vacuum sources for these devices are not being operated, smoke rises and can be inhaled by the operating surgeon and others in the operating room.

It has been found that the smoke generated during electrocautery surgery may be carcinogenic and/or otherwise injurious to those who may inhale the same. To Applicant's knowledge, no one has ever proposed a simple and inexpensive device which is primarily intended to remove smoke generated during electrocautery surgery to prevent a surgeon from inhaling the same.

Gas venting devices have been proposed for removing anesthetic gases or other fumes or dust from an operating room or a dental consultation room. Such devices are shown, for example, in U.S. Pat. Nos. 3,877,691; 4,082,092 and 4,446,861. Each of these devices shows a substantially rigid gas venting shield which is mounted at the end of a support arm so that the same can be positioned where needed. Again, however, these devices are relatively expensive and must be cleaned and sterilized after each use.

Masks have also been employed by surgeons and other operating room personnel to not only protect the patient but to also protect the operating personnel from airborne bacteria, viruses and the like. While simple cloth-filter type masks provide some benefit, they cannot prevent significant amounts of smoke and other dangerous gases from passing therethrough. Masks which include vacuum sources therein for protecting the doctor have been proposed in U.S. Pat. Nos. 3,747,599. Such a mask might have some practicality when there is only one doctor present during surgery but would become impractical if each person in the operating room were wearing one. Furthermore, as with the devices discussed above, the mask shown in this patent is relatively expensive and, again, must be cleaned and sterilized after each use.

SUMMARY OF THE INVENTION

The present invention is designed to overcome the deficiencies of the prior art devices described above and provides a very simple shield for use in an operating room for eliminating smoke created during electrocautery surgery so as to prevent injury to the operating physician and other operating room personnel. The shield is made from very inexpensive materials and is intended to be disposable. According to the invention, the shield is comprised essentially of an elongated base member and a concave wall which extends upwardly from one edge thereof. Located on the upper surface of the base member is an elongated suction tube which extends along the base member. A plurality of vertical openings in the upper surface of the tube create an air flow when the tube is connected to a vacuum source. Air and smoke in the vicinity of the shield are drawn inwardly toward the top of the shield, down the inner surface of the concave wall and into the suction tube. The bottom surface of the base member has a pressure sensitive adhesive thereon so that the shield can be mounted on a patient or on the patient's surgical gown or covering adjacent the surgical area.

BRIEF DESCRIPTION OF THE DRAWINGS

For the purpose of illustrating the invention, there is shown in the accompanying drawings one form which is presently preferred; it being understood that the invention is not intended to be limited to the precise arrangements and instrumentalities shown.

FIG. 4 is a front perspective view similar to FIG. 3 but showing the shield in its fully assembled condition;

FIG. 5 is a rear perspective view of FIG. 4, and

FIG. 6 is a cross-sectional view taken through the line 6—6 of FIG. 5.

DETAILED DESCRIPTION OF THE PREFERRED EMBODIMENT

Figure 1:
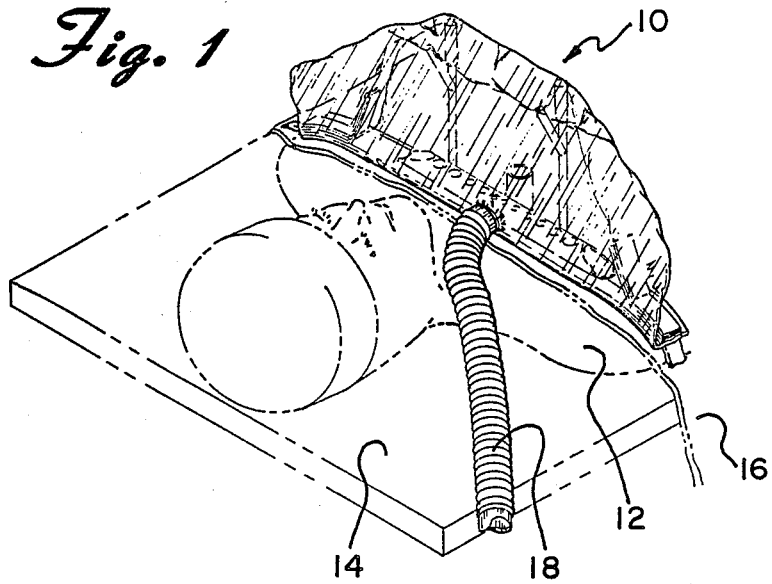
FIG. 1 is a rear perspective view of an electrocautery smoke eliminating shield constructed in accordance with the principles of the present invention and showing the same in use.

Referring now to the drawings in detail wherein like reference numerals have been used throughout the various figures to designate like elements, there is shown in FIG. 1 a rear perspective view of an electrocautery smoke eliminating shield constructed in accordance with the principles of the present invention and designated generally as 10. The shield 10 is shown secured to the upper chest portion of patient 12 lying on an operating table 14. Rather than being attached directly to the patient, the shield is actually secured to the cloth 16 draped over the patient A suction hose 18 connects the shield 10 to a vacuum source. With the shield 10 positioned in the manner shown in FIG. 1, the same is useful for removing smoke generated during electrocautery surgery on the patient's breast area.

Figure 2:
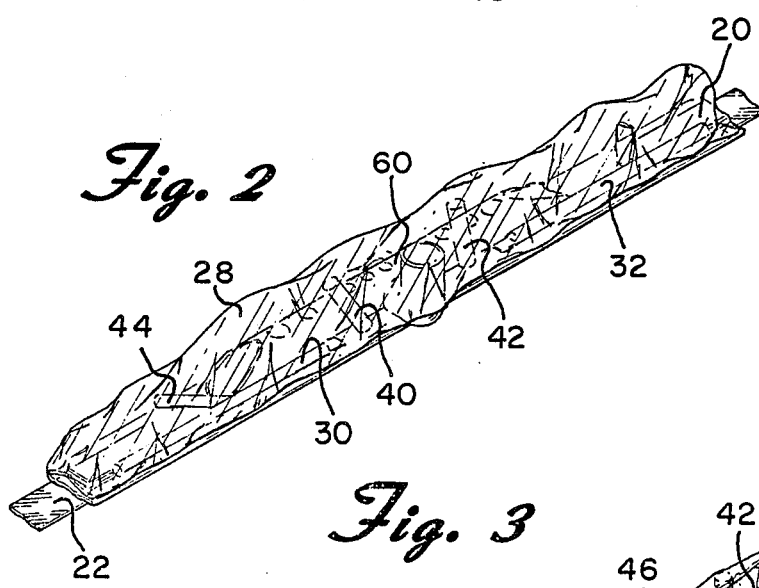
FIG. 2 is a perspective view of the inventive shield in its collapsed form prior to use.

The shield 10 which would normally be packaged and shipped in a collapsed form such as shown in FIG. 2 is comprised essentially of an elongated substantially flat and flexible base member 20. The bottom or lower surface of the base member 20 carries a tape 22 having a pressure-sensitive adhesive 24 on its lower surface.

Prior to use, the adhesive surface 24 is covered and thereby protected by a release paper which is removed when it is desired to utilize the shield.

Attached to the rear edge 26 is a substantially rectangularly shaped piece of sheet-like material 28. The sheet-like material is preferably made from a thin film of clear plastic such as polypropylene, polyethylene or the like.

Secured to the upper surface of the base member 20 are a pair of elongated and substantially rigid support members 30 and 32. The support members 30 and 32 are mounted to the left and right side of the middle of the base member by flexible connections 34 and 36 which allow the same to be pivoted from a horizontal position such as shown in phantom in FIG. 2 to the vertical position shown in the remaining figures.

Figure 3:
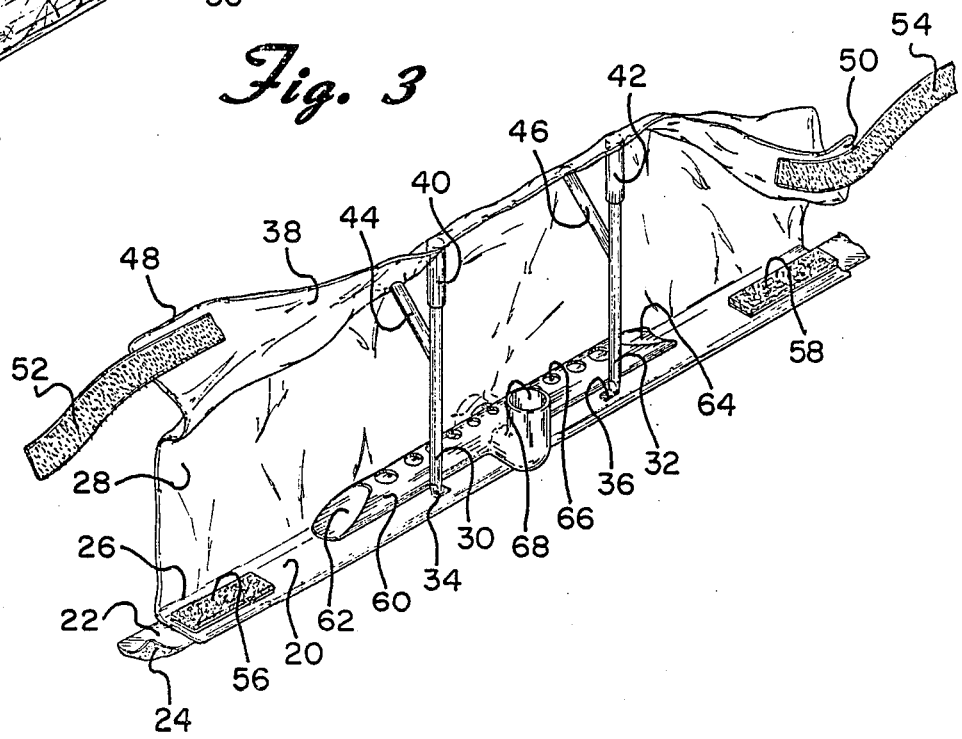
FIG. 3 is a front perspective view of the inventive shield in its partially assembled condition.

Secured to the free edge 38 of the flexible material 28 are plastic caps 40 and 42, each of which has its bottom open. With the supports 30 and 32 raised to their vertical positions as shown in FIG. 3 and with the sheet material 28 extended upwardly to form a rear wall, the upper ends of the support members 30 and 32 are fitted into the lower ends of the caps 40 and 42 in order to maintain the sheet material 28 in a vertically extending orientation. Rigid struts 44 and 46 are rigidly secured to the supports 30 and 32 adjacent the upper portion thereof and extend upwardly and rearwardly to engage the inside rear upper surface of the sheet-like material 28. The use of the supports 30 and 32 and the struts 44 and 46 thereby form the sheet-like material 28 into a rear wall having a substantially concave configuration as shown most clearly in FIG. 6.

The upper free corners of the sheet-like material 28 carry a strip of Velcro such as shown at 52 and 54. These Velcro strips are adapted to be attached to corresponding Velcro strips 56 and 58 mounted on the upper surface and at the ends of the base member 20 so that the front of the shield forms an inverted arc as shown most clearly in FIG. 4. Preferably the Velcro strips 52, 54, 56 and 58 are substantially long enough so that they can be connected to their respective complementary parts in various different locations. In the event, therefore, that the base member 20 must be bent arcuately downwardly or upwardly to conform to the patient's body, the Velcro strips can still be attached so that the shield will still have the downwardly curved arcuate opening substantially as shown in FIG. 4.

Also mounted on the upper surface of the base member 20 is an elongated suction tube 60. Tube 60 preferably extends throughout at least the central portion of the base member 20 covering approximately half of the overall length thereof. The ends 62 and 64 of the tube 60 are cut at an angle so as to form openings which face substantially upwardly an outwardly towards the upper corners of the shield.

The upper surface of the tube 60 is also provided with a plurality of openings therein such as shown at 66. The openings 66 are vertically oriented and increase in size from the center of the tube toward the ends 62 and 64 thereof. This arrangement tends to equalize the air pressure and flow along the length of the tube and through the various openings.

In addition to the openings 66 or in lieu thereof, the tube 60 may also be provided with a single large opening 68 located adjacent the center portion thereof. As shown most clearly in FIGS. 5 and 6, the central portion of the tube 60 is also provided with a coupler 70 which extends rearwardly through the rear wall formed by the flexible sheet-like material 28. Coupler 70 is adapted to be connected to the suction line 18 as shown in FIG. 1.

The shield 10 of the present invention is utilized in the following manner. When received, the shield is in the collapsed form as shown in FIG. 2. The flexible sheet-like material 28 is spread out and the supports 30 and 32 are pivoted into their vertical positions where the upper ends of the supports are inserted into the caps 40 and 42. At this point, the release paper is removed from the pressure-sensitive adhesive and the shield is placed on the patient's body with the front concave wall adjacent to and facing the area about to undergo electrocautery surgery. The Velcro strips 52, 54, 56 and 58 are then secured together and the suction hose 28 is connected to the coupler 70.

When the vacuum source is energized, air is pulled downwardly by the various openings in the suction tube 60 so that a downward draft is created along the inside rear concave wall of the shield. This is illustrated by the downwardly moving arrows in FIG. 6. Because of the top wall of the shield 10, air must be drawn inwardly in a horizontal direction adjacent the top of the shield to replace the air being drawn downwardly. This is illustrated by the substantially horizontal arrows shown in FIG. 6 which show air moving to the left. It can be seen, therefore, that any smoke or other gases rising from the area in front of the shield will tend to be drawn toward the top of the shield and then downwardly through the suction tube and will, essentially, follow the arrows shown in FIG. 6. Little, if any, of the smoke will rise above the top of the shield to be inhaled by the physician. This will be true even with a relatively weak vacuum source once the airflow pattern is created.

The present invention may be embodied in other specific forms without departing from the spirit or essential attributes thereof and accordingly reference should be made to the appended claims rather than to the foregoing specification as indicating the scope of the invention.

I claim:

1. A shield for eliminating smoke generated during electrocautery surgery comprising:
    an elongated substantially flat and flexible base member, said base member having a pressure sensitive adhesive on the lower surface thereof;
    a flexible sheet-like material attached to one edge of said base member and extending substantially upwardly therefrom;
    rigid support means connected to the upper surface of said base member and extending between said base member and the upper portion of said sheet-like material for maintaining said material in a substantially concave configuration;
    an elongated suction tube mounted on the upper surface of said base member and extending throughout at least the central portion thereof, said tube having a plurality of vertically oriented openings therein, and
    means for connecting said tube to a vacuum source to thereby create a flow of air from in front of said shield inwardly toward the top of the shield and down the inner surface of said material to said tube.

2. The invention as claimed in claim 1 further including means for connecting the upper corners of said sheet-like material to the ends of said base member.

3. The invention as claimed in claim 1 wherein said connecting means is centrally located with respect to said tube and wherein said openings increase in size from the center of said tube to the ends thereof.

4. The invention as claimed in claim 1 wherein said rigid support means are pivotally connected to said base member so that they can be pivoted between a lower inoperative position and an upper operative position.

5. The invention as claimed in claim 1 wherein said rigid support means are comprised of a pair of supports, each of said supports including a substantially vertically extending portion and a portion extending upwardly and rearwardly therefrom.

6. A shield for eliminating smoke generated during electrocautery surgery comprising:
    an elongated substantially flexible base member; adhesive means on the lower surface of said base member for securing the same to a patient;
    an upwardly extending concave wall connected to said base member;
    a rigid support means attached to said base member and extending between said base member and said concave wall;
    suction means associated with said wall for drawing air and smoke inwardly toward said wall.

7. The invention as claimed in claim 6 wherein said suction means is located adjacent the lower portion of said wall.

8. The invention as claimed in claim 7 wherein said suction means is comprised of a tube having a plurality of vertically oriented openings therein.

9. The invention as claimed in claim 6 wherein said wall is comprised of a flexible sheet-like material.

* * * * *